United States Patent [19]

Ensslin

[11] Patent Number: 4,662,369
[45] Date of Patent: May 5, 1987

[54] ELECTROSURGICAL APPARATUS HAVING A SAFETY CIRCUIT

[75] Inventor: Frieder H. Ensslin, Rochester, N.Y.

[73] Assignee: Castle Company, Rochester, N.Y.

[21] Appl. No.: 848,076

[22] Filed: Apr. 4, 1986

[51] Int. Cl.$^4$ ............................................. A61B 17/39
[52] U.S. Cl. ................................. 128/303.13; 128/908
[58] Field of Search ...................... 128/303.13, 303.14, 128/303.17, 908

[56] References Cited

U.S. PATENT DOCUMENTS

| | | | |
|---|---|---|---|
| 3,923,063 | 12/1975 | Andrews et al. | 128/303.17 |
| 4,094,320 | 6/1978 | Newton et al. | 128/303.14 |
| 4,188,927 | 2/1980 | Harris | 128/303.14 |
| 4,200,105 | 4/1980 | Gonser | 128/303.14 |
| 4,237,887 | 12/1980 | Gonser | 128/303.14 |
| 4,429,694 | 2/1984 | McGreevy | 128/303.14 |
| 4,437,464 | 3/1984 | Crow | 128/303.14 |
| 4,438,766 | 3/1984 | Bowers | 128/303.14 |

Primary Examiner—Lee S. Cohen
Attorney, Agent, or Firm—Marjama & Pincelli

[57] ABSTRACT

An electrosurgical device having a generator for producing a radio frequency current. The device senses an RF current leakage and thereby reduces the output of the RF generator so as to limit the amount of RF leakage to levels below a predetermined value.

4 Claims, 3 Drawing Figures

4,662,369

ELECTROSURGICAL APPARATUS HAVING A SAFETY CIRCUIT

FIELD OF THE INVENTION

This invention relates to electrosurgical devices and in more particular to means for minimizing the RF current leakage in an electrosurgical generator of the isolated type.

BACKGROUND OF THE INVENTION

Electrosurgery is a well-accepted technique for performing cutting and coagulation during surgical operations. Electrosurgical devices used for this purpose may be one of two types, one wherein the electrosurgical generator is grounded to the chassis of the device and the second being of the type wherein the generator is isolated from the chassis. The generator is generally capable of providing various types of high frequencies at various wave forms and power levels so as to provide various output signals at the active electrode for such techniques as cutting, coagulation, fulguration, or desication. The high frequency energy supplied by the generator is conveyed to the patient by the use of an active electrode. The Radio Frequency (RF) current is then returned to the generator through a return plate attached to the patient which generally has a large contact area. A large contact area reduces the current density flowing from the patient so as to minimize potential electrically burns occuring at the point of contact between the return plate and patient.

During use of electrosurgical device, there exists the possibility that the patient can suffer severe electrical burns if the radio frequency current returns to the electrosurgical device in an alternate route other than the return electrode via ground. There is also a possibility that others in the operating vicinity who are grounded may inadvertently touch the patient thereby causing burns to this other individual as well as to patient.

SUMMARY OF THE INVENTION

Applicants have found a novel way for minimizing the undesirable radio frequency current leakage to go around (RF leakage) that may occur in an electrosurgical device having an isolated generator. A device made in accordance with the present invention is provided with a first sensing capacitor having one end connected to the active output lead and a second sensing capacitor having one end connected to the return output lead. The capacitors have sufficienty low value so as not to cause an appreciable ground reference connection. The other ends of both sensing capacitors are connected to each other and to the primary side of a sensing transformer. The other end of the primary side of the sensing transformer is connected to chassis ground. The electrosurgical device has an inherent first leakage capacitance between the active output lead and chassis ground and a second inherent leakage capacitance between the return lead and chassis ground. The values for the first and second sensing capacitors are selected such that an externally caused imbalance between the inherent leakage capacitance and sensing capacitors will generate a signal which will control the power output of the generator such that the RF leakage current will not be permitted to go above a pre-determined set value.

DETAILED DESCRIPTION

Figure 1:
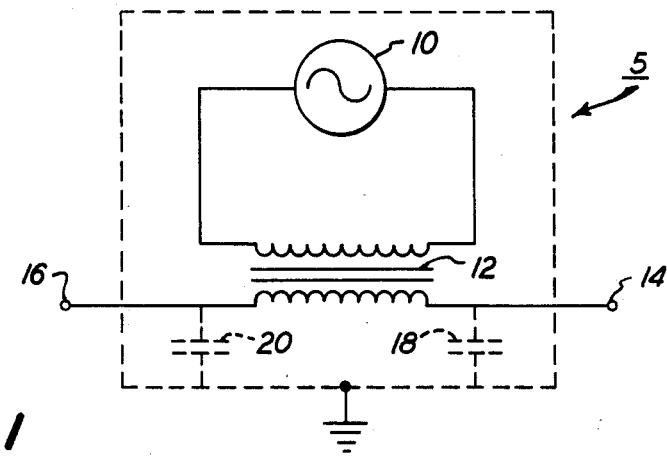
FIG. 1 is a diagram, partly in block and schematic form illustrating the basic electrical representation of an electrosurgical generator isolated from the chassis of an electrosurgical device.

FIG. 1 is a diagram of a prior art electrosurgical unit 5 having a generator 10 wherein the output is connected to the primary side of transformer 12. The secondary side of transformer 12 is connected to the active electrode 14 and return electrode 16. The chassis ground of electrosurgical device 5 is illustrated by dash lines connected to ground. Electrosurgical device 5 will have a inherent first leakage capacitance 18 between the active electrode 14 and the chassis ground and a second inherent leakage capacitance 20 between the return electrode and chassis ground.

Figure 2:
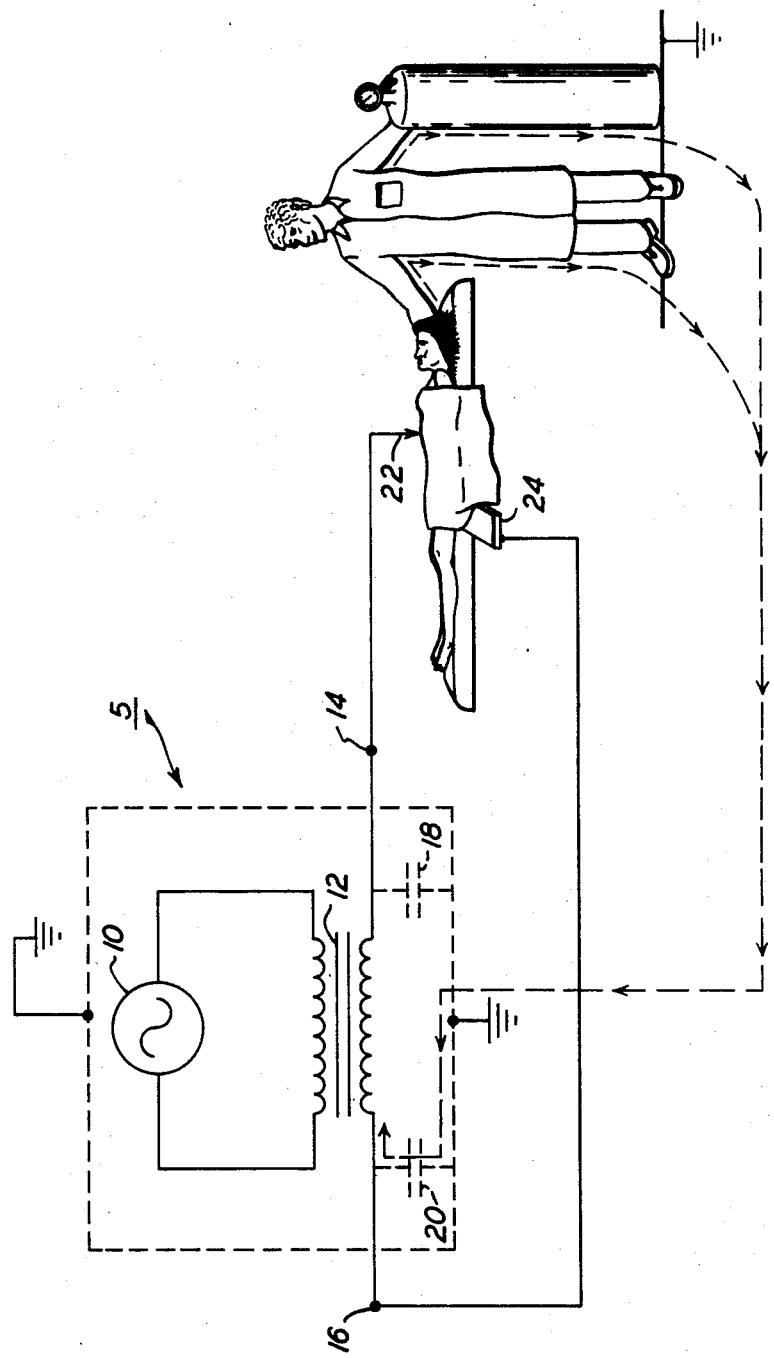
FIG. 2 is a diagram identical to FIG. 1 illustrating a situation which may result in burns to the patient and other person in the operating vicinity.

Referring to FIG. 2 there is illustated the device of FIG. 1 wherein at least a portion of the RF current is returned to the generator via a route different than through the return electrode, which may result in burns to the patient. During normal operation the RF current goes from active electrode 14 to handpiece 22, which is generally held and operated by a surgeon. The RF current travels through the patient to ground plate 24 and then back to return electrode 16. However, in the situation illustrated in FIG. 2 at least a portion of the RF current being delivered at handpiece 22 is being returned by an alternate undesirable ground route. In this particular situation RF current is transmitted through a person who is in contact with the patient, e.g. an anesthesiologist, who is either directly grounded or is in contact with an object that is grounded. In the situation illustrated the anesthesiologist is directly grounded and is also touching a metal tank that is grounded. The dash arrow line indicates that the RF current leakage returns to the device 5 through ground to the return side of transformer 12 through leakage capacitor 20. The foregoing is only illustrative as to two alternate ground routes potentially available. Various other undesirable ground routes are potentially possible.

Figure 3:
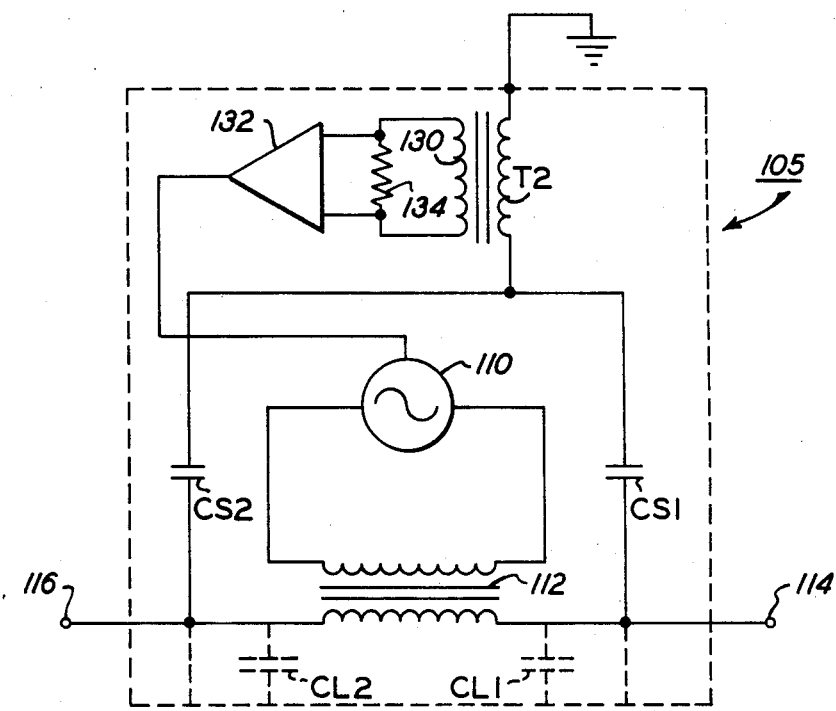
FIG. 3 is a diagram, partly in block and schmatic illustrating the safety circuitry of the present invention.

Referring to FIG. 3 there is illustrated, partly in block and schematic, an electrosurgical device 105 made in accordance with the present invention. The electrosurgical device has an electrosurgical generator 110 separated from chassis ground and having its output connected to a transformer 112. The transformer 112 has an active electrode or lead 114 for supplying the RF frequency current to the handpiece normally held by the surgeon. The secondary side of the transformer 112 also has a return electrode or lead 116 which is connected to the ground plate attached to the patient. Chassis ground of the electrosurgical device of the present invention is indicated by the dash lines. Electrosurgical device 105 due to its design and construction will have an inherent first leakage capacitance CL1 between the active electrode 114 and chassis ground and an inherent second leakage capacitance CL2 between the return electrode 116 and chassis ground. A first sensing capacitor CS1 having a predetermined value is provided having one lead connected to the active electrode 114. A second sensing capacitor CS2 having a second predetermined value is provided having one lead connected to a return electrode 116. The other end of sensing capacitor CS1 and CS2 are connected to each other which are in turn electrically connected to one lead on the primary side of a sensing transformer T2. The other lead of the sensing transformer T2 is connected to chassis ground. The secondary side 130 of sensing transformer T2 is connected to a amplifier 132 and resistor 134. The amplifier is electrically connected to the generator 110 and produces a signal for reducing the output of the generator 110 until the RF current leakage is below a predetermined value. In the preferred invention the values for the amplifier 132 and resistor 134 are selected such that the RF current leakage will be kept below approximately 150 milliamps into 200 ohms which is equivalent to 4.5 watts.

As can be seen from FIG. 3, leakage capacitance CL1, CL2 and sensing capacitors CS1 and CS2 are electrically connected so as to provide a bridge circuit which can sense an imbalance between the RF current being provided at active electrode 114 and the RF current returning at return electrode 116. The values for CS1 and CS2 are sufficiently low so as not to constitute an appreciable ground reference connection. The capacitance values for CS1 and CS2 are selected such that the following relationship is satisfied:

$$CL1/CS1 = CL2/CS2$$

wherein:
  CL1 = first leakage capacitance between the active electrode and chassis ground
  CL2 = second leakage capacitance between the return electrode and chassis ground
  CS1 = first sensing capacitor between the active electrode and sensing transformer
  CS2 = second sensing capacitor between the return electrode and sensing transformer When the foregoing relationship is satisfied no current flow will occur through the primary side of sensing transformer T2, therefore there will be no negative feedbacks supplied to the RF generator. This condition prevails for any load connected between leads 114 and 116. However, if a load appears from lead 114 or lead 116 to chassis ground, the bridge circuit will become imbalanced and will generate a negative feedback control signal to the radio frequency generator for reducing its output to power levels that will not produce RF current leakages higher than desired by the designer which is a function of the gain selected in the negative feedback loop. Means are provided for limiting the power output of the generator 10 using the output signal of the amplifier, such means are well known to those of the ordinary skill in the art.

Various other modifications may be without departing from the scope of the present invention. For example, if desired a warning light or other signal means can be placed at the output of the amplifier to alert the user of the electrosurgical device that it is experiencing an RF current leakage. Additionally, the resistor 134 and the type of amplifier 132 used may be varied as desired by the designer.

What is claimed is:

1. An electrosurgical device having a chassis ground, comprising a radio frequency generator having its output connected to an output transformer having an output lead and return lead;
  a first leakage capacitance between said output lead and said chassis ground;
  a second leakage capacitance between said return lead and said chassis ground;
  means for sensing RF current leakage in said electrosurgical device comprising a sensing transformer having a primary side and secondary side, said primary side having a first and second leads, said first lead of said primary side of said sensing transformer being connected to said chassis ground, a first sensing capacitor being electrically connected between said output lead and second lead of said primary side of said sensing transformer, a second sensing capacitor electrically connected between said return lead and said second lead of said primary side of said sensing transformer, said secondary side of said sensing transformer producing a signal in response to said RF current leakage in said device, means for limiting the power output of said generator in response to said signal reducing said RF current leakage below a predetermined value.

2. An electrosurgical device according to claim 1 further characterized by said secondary side of said sensing transformer produces a signal in response to the following relationship:

$$CL1/CS1 = CL2/CS2$$

wherein:
  CL1 = said first leakage capacitance
  CL2 = said second leakage capacitance
  CS1 = said first sensing capacitor
  CS2 = said second sensing capacitor.

3. An electrosurgical device according to claim 1 further characterized by said means for limiting the power output of said generator comprises an amplifier connected to a said secondary side of said sensing transformer, the output of said amplifier produces a negative feedback control signal in response to the RF current leakge for controlling the output of said generator.

4. An electrosurgical device having chassis ground comprising a radio frequency generator having its output connected to an output transformer having an output lead and a return load, said device having a first leakage capacitance between said output lead and said chassis ground and a second leakage capacitance between said return lead and chassis ground, means for sensing RF current leakage in said electrosurgical device comprising: a first sensing capacitor is provided having first and second leads, said first lead of said first sensing capacitor being connected to said output lead of said generator, a second sensing capacitor is provided having a first and second connecting leads wherein said first lead of said second sensing capacitor is connected to said return lead of said generator, said second leads of said first and second capacitors being connected to each other, means for sensing an electrical imbalance between said first and second leakage capacitances and said first and second sensing capacitors which follow the relationship:

$$CL1/CS1 = CL2/CS2$$

wherein:
  CL1 = said first leakage capacitance
  CL2 = said second leakage capacitance
  CS1 = said first sensing capacitor
  CS2 = said second sensing capacitor
means for reducing the output of said generator in response to said electrical imbalance between said first and second leakage capacitances and the first and second capacitors so that RF current leakage will be kept below a predetermined set value.

* * * * *